(12) United States Patent
Eger et al.

(10) Patent No.: US 9,238,114 B2
(45) Date of Patent: Jan. 19, 2016

(54) PROCESS FOR THE AUTOMATIC CONTROL OF A RESPIRATOR

(75) Inventors: Marcus Eger, Lübeck (DE); Hans-Ullrich Hansmann, Barnitz (DE); Tobias Glaw, Lübeck (DE); Frank Sattler, Lübeck (DE); Thomas Handzsuj, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1154 days.

(21) Appl. No.: 13/194,200

(22) Filed: Jul. 29, 2011

(65) Prior Publication Data

US 2012/0152251 A1 Jun. 21, 2012

(30) Foreign Application Priority Data

Dec. 20, 2010 (DE) .......................... 10 2010 055 243

(51) Int. Cl.
*A61M 16/00* (2006.01)

(52) U.S. Cl.
CPC ............ *A61M 16/0051* (2013.01); *A61M 16/00* (2013.01); *A61M 16/0003* (2014.02); *A61M 2016/0015* (2013.01); *A61M 2205/33* (2013.01); *A61M 2205/50* (2013.01); *A61M 2230/40* (2013.01)

(58) Field of Classification Search
CPC ...... A61B 5/0488; A61B 5/807; A61B 5/091; A61M 16/0051; A61M 2230/60; A61M 2230/005; A61M 2230/08; A61M 16/00; A61M 16/0003; A61M 2016/0015; A61M 2205/33; A61M 2205/50; A61M 2230/40

USPC .......................... 128/200.24, 204.18–204.23, 128/204.26–204.28, 205.13–205.19, 128/205.23–205.25, 207.14–207.17, 898; 600/529, 534–536

See application file for complete search history.

(56) References Cited

U.S. PATENT DOCUMENTS

| | | | |
|---|---|---|---|
| 5,598,838 A * | 2/1997 | Servidio et al. .......... | 128/204.23 |
| 6,588,423 B1 | 7/2003 | Sinderby | |
| 6,626,176 B1 * | 9/2003 | Madaus et al. ............ | 128/204.23 |
| 7,255,103 B2 * | 8/2007 | Bassin ...................... | 128/204.18 |
| 8,109,269 B2 * | 2/2012 | Eger ......................... | 128/204.23 |
| 2006/0272641 A1 | 12/2006 | Madaus et al. | |
| 2008/0275349 A1 * | 11/2008 | Halperin et al. .............. | 600/484 |
| 2008/0283060 A1 | 11/2008 | Bassin | |

(Continued)

FOREIGN PATENT DOCUMENTS

| | | |
|---|---|---|
| DE | 101 03 810 A1 | 8/2002 |
| DE | 102 12 497 A1 | 10/2003 |
| DE | 10 2007 062 214 B3 | 8/2009 |

OTHER PUBLICATIONS

Merlett, R., Parker P. A.: Electromyography Physiology, Engineering, and Noninvasive Applications. IEEE Press, Wiley Interscience, 2004, starting from chapter 6.4 or pp. 139 ff.
European Examination Report of Jun. 3, 2015.

*Primary Examiner* — Annette Dixon
*Assistant Examiner* — Mark K Han
(74) *Attorney, Agent, or Firm* — McGlew and Tuttle, P.C.

(57) ABSTRACT

A process for automatic control of a respirator changes between two phases of respiration by checking a detected respiratory breathing activity signal for a threshold criterion. If the threshold criterion is met, a changeover is made.

20 Claims, 3 Drawing Sheets

(56) References Cited

U.S. PATENT DOCUMENTS

| | | |
|---|---|---|
| 2009/0159082 A1 | 6/2009 | Eger |
| 2010/0083968 A1 | 4/2010 | Wondka et al. |
| 2010/0180898 A1 | 7/2010 | Schneider et al. |
| 2010/0252038 A1 | 10/2010 | Lagerborg et al. |
| 2012/0116194 A1 * | 5/2012 | Gross et al. .................. 600/324 |

* cited by examiner

PROCESS FOR THE AUTOMATIC CONTROL OF A RESPIRATOR

CROSS REFERENCE TO RELATED APPLICATIONS

This application claims the benefit of priority under 35 U.S.C. §119 of German Patent Application DE 10 2010 055 243.7 filed Dec. 20, 2010, the entire contents of which are incorporated herein by reference.

FIELD OF THE INVENTION

The present invention pertains to a process for the automatic control of a respirator (ventilator) to change over alternately between two phases of respiration (inspiration and expiration) by a control unit checking a detected respiratory breathing activity signal in a phase of respiration for a threshold criterion for changing over into the next phase of respiration, and if the threshold criterion is met, a changeover is made from one phase of respiration into the other.

BACKGROUND OF THE INVENTION

Artificial respiration with respirators is aimed at relieving the respiratory muscles of a patient and at guaranteeing a sufficient supply of oxygen and elimination of carbon dioxide. This can happen by complete takeover of the breathing activity by the respirator or in an assisting process by partial takeover of breathing activity by the respirator, whereby in the latter assisting process, a present breathing activity of the patient is assisted or reinforced. For this, the respirators contain a fan for supplying breathing gas with a pressure, which is preset by a control unit. Furthermore, sensors are present, which detect pneumatic breathing signals in a time-dependent manner, for example, airway pressure, volume flow (flow) of the breathing gas and volume (which results from the integration of the flow), and forward these to the control unit.

In view of the rise in chronic lung diseases and the demand for an improved therapy, noninvasive breathing assistance with improved interaction of the patient and fan is a decisive requirement of modern respirators. An essential object herein is to establish time-based synchronicity between the device-side assistance and the patient's own breathing activity. Spontaneously breathing patients were frequently sedated in the past to adjust the respiration correctly and to force synchronicity between patient and respirator. This procedure is no longer acceptable by today's knowledge since risks of lung damage caused by the respiration have to be dealt with.

For an improved synchronization between the breathing activity of the patient and the fan action, it is important to detect the beginning of inspiration and the beginning of expiration in the breathing activity of the patient early and reliably. The breathing phase detection is especially often incorrect or late in newborns and in Chronic Obstructive Pulmonary Disease (COPD) patients using conventional processes and leads to increased respiratory work until exhaustion.

For an artificial respiration which shall take the patient's breathing activity into consideration in an improved manner, it is known from DE 10 2007 062 214 B3 to pick up electromyographic signals, besides pneumatic breathing activity signals, by means of electrodes placed on the thorax and to derive electromyographic breathing activity signals (EMG signals) therefrom. These EMG signals are independent of the pneumatic breathing activity signals and therefore represent an independent source of information, which can be used to detect the beginning of inspiration and expiration. The EMG signals are, however, not infrequently superimposed by interference, for example, the ECG signal of the heart, motion artifacts or so-called cross-talk (muscle activity that has nothing to do with the respiratory system of the patient).

A triggering of breaths on the basis of EMG signals is described in U.S. Pat. No. 6,588,423 B1. Here, the EMG raw signal is preprocessed and is finally used for triggering an intensity indicator (root mean square) of the EMG signal, whereby a fixed threshold is used—related to one breath.

In practice, however, the preprocessed EMG signal is often more susceptible to interference than pneumatic signals (pressure or volume flow). Such a susceptibility to interference or volatility makes it more difficult to change over or trigger the breaths when using trigger thresholds, since too many breaths may be mistakenly triggered (so-called autotrigger) or may be triggered too late (so-called delayed or missed trigger).

Marking of the signals with interference can be avoided by suitable filterings (e.g., by means of sliding averaging) of the signals. However, this would result in the major drawback of an additional signal delay for the intended use for changing over between phases of respiration.

In DE 102 12 497 A1, it is generally pointed out that at the beginning of a phase of inspiration, a continuation of the inspiration phase is essentially more likely than its premature end, and that a new beginning of an inspiration phase has a higher probability shortly before an end of the phase of expiration. Basically, it means that with an increasing probability for the development of an event triggering the phase of respiration, the trigger threshold can be lowered, since the influence of interference is unlikely, on the one hand, and moreover, even in case of a mistriggering based on a developing interference, the result of this erroneous changeover is markedly less interfering because of the chronological closeness to a correct changeover point in time than an erroneous changeover at a completely incorrect point in time. Moreover, no further indications are, however, made as to how and with what time curve and up to what chronological point in time a dynamic threshold curve shall be performed chronologically.

SUMMARY OF THE INVENTION

An object of the present invention is to provide a process for the automatic control of a respirator, which, on the one hand, makes possible a sensitive changeover into the next phase of respiration, and, on the other hand, keeps incorrect changeovers from inspiration into expiration or from expiration into inspiration as low as possible by using a well-adapted dynamic threshold at the instantaneous respiration situation.

According to the present invention, in an expiration phase, a dynamic threshold curve $u_{insp,thresh}(t)$ is used for changing over into an inspiration phase, which, after the beginning of the present expiration phase holds the threshold at high values for a selected inspiratory refractory period, i.e., up to a point in time $t_{i1}$ such that a changeover into inspiration is impossible at such an early point in time. Then, the threshold curve is lowered monotonically, dropping to an inspiratory threshold target value at the expected phase duration maximum $t_{i2}$ and changed over into the inspiration phase, as soon as the breathing activity signal exceeds the threshold curve for inspiration.

In an inspiration phase, a dynamic threshold curve $u_{exp,thresh}(t)$ is used for the changeover into an expiration phase, which is held at such low values after the beginning of the present inspiration phase for a selected short expiratory refractory period, i.e., up to the point in time $t_{e1}$ that a changeover into expiration is impossible in this early phase. Then, the threshold curve is raised monotonically, increasing to an expiratory threshold target value at the expected phase duration maximum $t_{e2}$ and changed over into the expiration phase, as soon as the breathing activity signal drops below the threshold curve via the expiration. Points in time of the end of the inspiratory refractory period $t_{i1}$ and/or the expiratory refractory period $t_{e1}$ may each derived from distributions of the phase durations of the inspiration and expiration phases as a p-quantile of the distributions, whereby the p-quantile values used here $p_{i1}$ and $p_{e1}$ are selected beforehand and have values of less than 1.

In this context, the phase durations of the respective inspiration and expiration phases or the breath duration (sum of inspiration phase and expiration phase for one breath) are stored. The expected phase duration maxima $t_{i2}$ and $t_{e2}$ can be derived from the distributions of the phase durations (in relation to the beginning of the respective phase of respiration) or from the distribution of breath durations (in relation to the beginning of the previous phase of respiration), and preferably as a p-quantile of the distribution, whereby the parameter P is fixed beforehand and has a high value close to 1, i.e., 0.95, which means that the point in time of the expected phase duration maximum is set such that the actual phase end was already reached at this point in time in 95% of the cases of the previous phases of respiration. As an alternative, a Gaussian distribution can be assumed, and the expected phase duration maximum can be fixed at a preset number of standard deviations above the mean value in this distribution, e.g., 2.5 $\sigma$. Parameters $P_{i2}$ and $P_{e2}$ may be determined for quantiles beforehand, and parameter values $P_{i2}$ and $P_{e2}$ are at least 0.8.

The points in time of the end of the inspiratory and expiratory refractory periods $t_{i1}$ and $t_{e1}$ and the expected phase duration maxima $t_{i2}$ and $t_{e2}$ can be related, as a time zero point, to the point in time of the changeover into the present phase of respiration. As an alternative, the pattern of the breathing activity signal can be stored over at least the duration of one phase of respiration and the beginning of the present phase of respiration can be determined later by examining the pattern of the breathing activity signal in a period about the point in time of the changeover into the present phase of respiration. Based on a more accurate examination of the signal pattern of the breathing activity signal, the actual beginning of the present phase of respiration can later be determined more accurately than in real time of the triggering point in time of the changeover of the respirator. Median values $t_{im}$ and $t_{em}$ also arise from the distributions of the phase durations as 0.5-quantiles, which can be considered to be expected values for phase durations of inspiration and expiration.

The threshold target value is determined from the amplitude distributions of the breathing activity signals at the point in time of the mean phase durations $t_{im}$ and $t_{em}$, whereby $t_{im}$ is the median value of the inspiratory phase durations and $t_{em}$ is the median value of the expiratory phase durations. In the amplitude distributions at these points in time, the threshold target values can be fixed as a p-quantile, or assuming a Gaussian distribution, as a (generally nonintegral) multiple of the standard deviation relative to the mean value. For example, the inspiratory threshold target value can be fixed as a 0.05-quantile in the amplitude distribution at the point in time $t_{im}$, i.e., the threshold target value is such that 95% of the breathing activity signal amplitudes lie above the threshold target value at the point in time $t_{im}$. The expiratory threshold target value can be fixed as a 0.95-quantile in the amplitude distribution at the point in time $t_{em}$, i.e., the threshold target value is such that 95% of the breathing activity signal amplitudes lie below the expiratory threshold target value at the point in time $t_{em}$.

In a preferred embodiment of the process, the values of the breathing activity signal are stored at a plurality of points in time during the inspiration $t_i^j \in [t_{i1}, t_{im}]$ (j=1, ... n) and during the expiration $t_e^k \in [t_{e1}, t_{em}]$ (k=1, ... n) and stored at this plurality of points of time as amplitude distributions of the signal values of the breathing activity signal. These amplitude distributions can be used in the following manner for guiding the threshold curve to the threshold target value. For this, at first use is made of the fact that the distribution of the phase durations corresponds to a probability density, which can be converted (by integration) into a distribution function V(t) which then increases from the lowest point of the density function (the shortest observed phase duration) from 0 to the utmost endpoint of the distribution (the longest observed phase duration) to 1. The respective value of this distribution function indicates with what probability a changeover should be made into the next phase of respiration up to a respective point in time. The probability of changeover increasing over time can be extrapolated to a plurality of consecutive points in time in correspondingly decreasing thresholds in the amplitude distributions of the breathing activity signal, such that the probability of changeover after the distribution function of the phase durations follows the probability, with which the threshold criterion for changeover is met after the amplitude distribution.

For example, the thresholds can be placed in the amplitude distributions, such that the distribution function of the phase durations V(t) at the plurality of points in time $t_i^j \in [t_{i1}, t_{im}]$ and $t_e^k \in [t_{e1}, t_{em}]$ defines a p-quantile criterion in the breathing activity signal distributions, wherein p is a function of V(t), p=F(V(t)). Here, F(V(t)) is a function of the distribution function, which generally varies essentially linearly with the distribution function, in the simplest case the identity F(V(t))=V(t) for expiration and the reflection F(V(t))=1−V(t) for inspiration.

As an alternative, the thresholds can be placed as a (generally nonintegral) number $A(V(t_i^j))$ and $A(V(t_e^k))$ of standard deviations relative to the mean value of a Gaussian distribution, such that the probability of phase end after the distribution of the phase durations corresponds to the probability of meeting the threshold criterion in amplitude distributions. A(V(t)) is a predetermined function, which fixes the number of standard deviations, such that the probability of the phase end after the distribution of the phase durations corresponds to the probability of meeting the threshold criterion in the amplitude distributions. This function can, e.g., be selected, such that the probability of the phase end after the distribution function of the phase durations V(t) at a point in time t follows the probability of meeting the threshold criterion in the amplitude distribution, for which the (tabulated) Gaussian error integral:

$$\Phi(u) = 1/(\sigma\sqrt{2\pi}) \int_{-\infty}^{u} e^{-\frac{1}{2}(\frac{x}{\sigma})^2} dx$$

can be used, which indicates with what probability in a Gaussian distribution a value lies above a value u. E.g., 68% of the entries in a Gaussian distribution lie above 1s, 95% within 2s and 99.7% within 3$\sigma$ ($\sigma$=standard deviation).

As an example, the function F(V(t))=1−V(t) is set in inspiration and F(V(t))=V(t) in expiration. In the histograms of the amplitude distributions of the breathing activity signal at the times $t_i^j \epsilon [t_{i1}, t_{im}]$ and $t_e^k \epsilon [t_{e1}, t_{em}]$, the thresholds are then placed, such that they fix a $(1-V(t_i^j))$-quantile in the amplitude distribution in inspiration and a $V(t_e^k)$-quantile in expiration. For example, the first point in time after $t_i^1$ from the plurality of points in time would be, such that the value of the distribution function $V(t_i^1)$ is then 0.05 (corresponding to 5%), which corresponds to a probability of 5% for an actual phase end. In the associated amplitude distribution of the breathing activity signal at this point in time, the threshold in this example is now fixed such that it forms a (1-0.05)-quantile, i.e., 5% of the amplitudes lie above the fixed inspiratory threshold and 95% lie below same. At a next point in time $t_i^2$, the value of the distribution function of the phase durations would now be 0.25. Then, the inspiratory threshold in the amplitude distribution at this next point in time is set as a (1-0.25)- or 0.75-quantile, such that 25% of the amplitude values lie above the threshold and 75% lie below same. The threshold is thus set, such that the probability of changeover into the next phase of respiration follows the probability that arises for a phase end from the distribution of the phase durations exactly. This process is continued until the value of the distribution function of phase durations has reached 0.5, which then corresponds to a threshold in amplitude distributions at this point in time with a p-quantile value with p=0.5.

In the intervals between the points in time from the plurality of points in time, the threshold curve can be interpolated, or the threshold curve can in each case be guided linearly to the threshold value at the next point in time from the plurality of points in time.

The threshold is subsequently lowered to the threshold target value, which can be derived from the amplitude distribution at the point in time, at which the distribution function of the phase durations has the value 0.5, i.e., the distribution at any point in time is also used as the basis in the period, after the distribution function has reached the value 0.5, and the threshold is now lowered to the threshold target value in this distribution. This threshold target value is, as described above, fixed as a p-quantile in the amplitude distribution at the point in time $t_{im}$, e.g., as a 0.05-quantile, which means that 95% of the breathing activity signal amplitudes at the point in time $t_{im}$ lie above the threshold target value. This process is based on the consideration that increasing breathing activity signals from incipient inspirations are already contained after the average phase duration (which corresponds to the value of the distribution function of 0.5), such that the distributions contain increasing influences of new phases of respiration already begun again and thus no longer reflect the behavior at the end of running phases of respiration with very long phase durations.

Here as well, guiding to the target value may take place via a plurality of support points, i.e., at a plurality of points in time from the interval $[t_{i1}, t_{im}]$ or $[t_{e1}, t_{em}]$, the threshold is guided, e.g., as a (1-V(t))-quantile in the amplitude distribution for the point in time $t_{im}$ for the inspiratory threshold and as a V(t)-quantile in the amplitude distribution for the point in time $t_{em}$ for the expiratory threshold. The threshold curve can in turn be interpolated between the points in time from the plurality of points in time.

The present invention is explained below based on the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
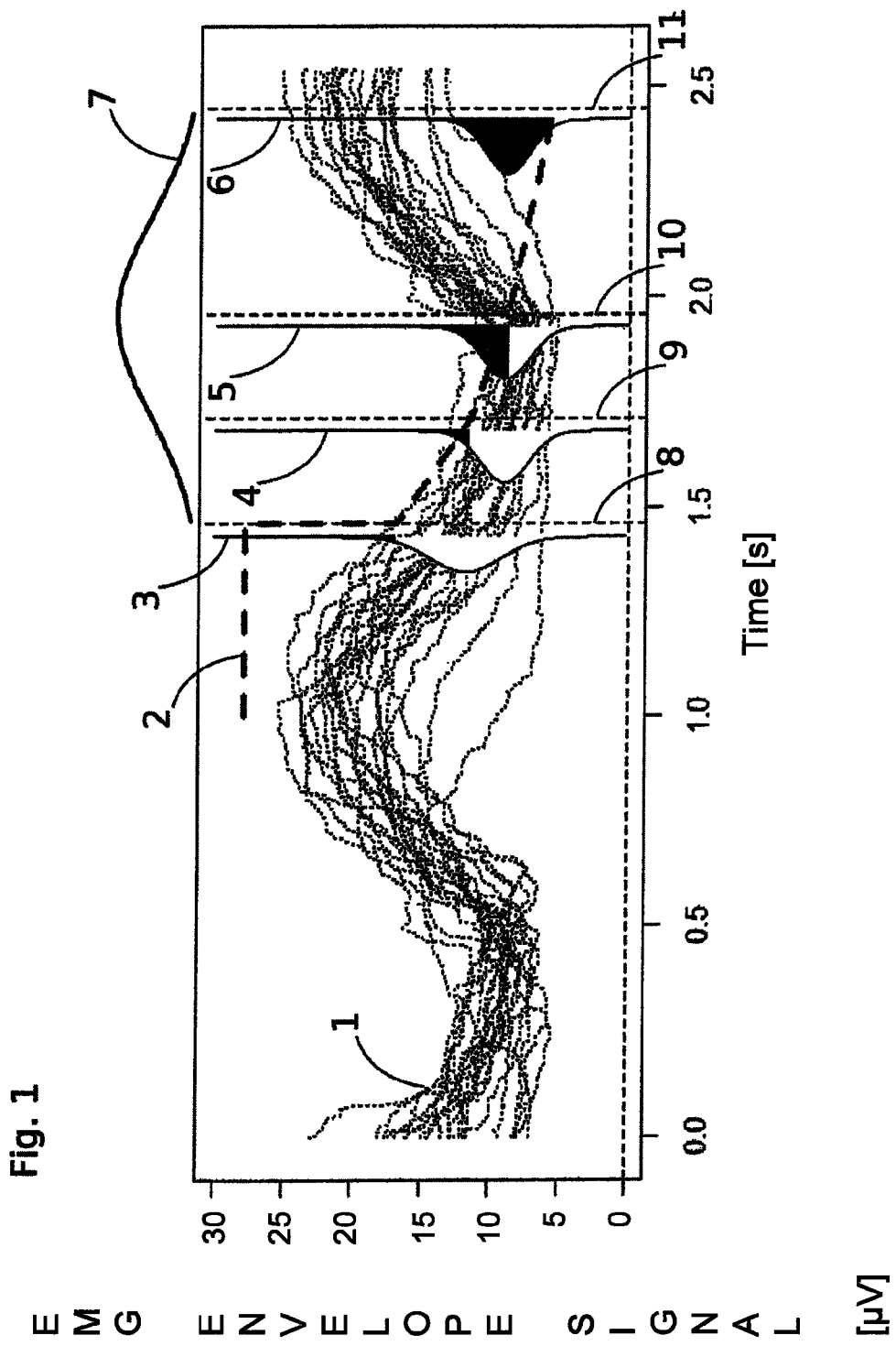
FIG. 1 is a graph showing breathing activity signals as a function of time, which are superimposed for a multiple of breathing cycles.

Referring to the drawings in particular, an electromyographic signal (EMG signal), which is picked up via electrodes on the thorax and which represents the muscle activity associated with breathing, is used as a breathing activity signal in the present example.

A preprocessed EMG signal is preferably used. Such a preprocessing of the EMG raw signal takes place in the known manner in such a way that the EMG raw signal is freed from interference signals (e.g., ECG, motion artifacts, humming) and finally an envelope detection is performed. An envelope detection may be done, for example, by "rectification" and subsequent low-pass filtering, whereby the "rectification" is done by an operation imaging the quantity (e.g., by squaring or pure quantity formation). After a low-pass filtering, the envelope is then obtained, i.e., the curve enveloping the signal pattern of the raw signal. A preferred realization of envelope detection is the formation of the so-called RMS (Root Mean Square) over the length of a sliding time window. The concept of EMG amplitude estimation, which is defined by the term "envelope detection," is described in detail in Merlett, R., Parker P. A.: Electromyography. Physiology, Engineering, and Noninvasive Applications. IEEE Press, Wiley Interscience, 2004, starting from chapter 6.4 or pages 139 ff.

Such an EMG envelope signal was picked up via a plurality of breathing cycles and superimposed in the view shown in FIG. 1. In this case, the individual signals were superimposed, such that the exact point in time of the beginning of inspiration (at about 1.9 sec in FIG. 1) arising after the beginning of inspiration by examining the previous breathing activity signal is set at a common point in time, and in this respect the consecutive phases of respiration are "synchronized" in the view shown in FIG. 1.

According to the present invention, in an expiration phase (dropping breathing activity signal), a dynamic threshold curve for the changeover into the next inspiration phase is used, which is held at high values, a high constant value in this example, after the beginning of the present expiration phase for a selected inspiratory refractory period, i.e., up to a point in time $t_{i1}$, in order to prevent a premature changing over into inspiration. This threshold curve is designated by 2 in FIG. 1. The inspiratory refractory period is a preselected or, as explained further below, short period of time determined from the breathing activity signals which begins with the beginning of the expiration phase and ends at the point in time $t_{i1}$, and which is so short that the beginning of a new inspiration is extremely unlikely after such a short time since the beginning of expiration. If a preselected value is used, the inspiratory refractory period may be, for example, 200 msec. During this time, threshold 2 is held at such a high value that a changeover into inspiration is practically ruled out.

After the inspiratory refractory period, the threshold is lowered, so that an optimal threshold value is fixed for triggering the next correct inspiration. For this, at first the distribution of the expiratory phase durations is observed, which is indicated by 7 in FIG. 1. This distribution 7 represents the probability density, which can also be shown integrated as a distribution function V(t), as shown at the top in FIG. 2. The distribution function corresponding to the probability density 7 would in FIG. 1 increase then from the point in time, designated by 8, from a very small value (which is determined by the p-quantile, which, as described above, was used to determine the inspiratory and expiratory refractory periods) up to the point in time, designated by 11, to a value close to 1 (which is determined by the p-quantile, which, as described above, was used to determine the phase duration maxima), i.e., the probability that the next inspiration begins increases in this time interval correspondingly. The curve of the distribution function V(t) is designated by 12 in FIG. 2 at the top.

In the preferred embodiment, the amplitude distribution of the breathing activity signal is stored at a plurality of points in time in the interval between the end of the inspiratory refractory period $t_{i1}$ and the point in time of the mean expected phase duration $t_{im}$ (median value of the distribution 7, designated by 10 in FIG. 1); in FIG. 1 there are three points in time 8, 9 and 10, for example. In the histograms 3, 4 and 5 of the amplitude distributions at these points in time, the threshold is now set in each case, such that the threshold for the inspiratory changeover corresponds to a p-quantile with the parameter $p=1-V(t_i^j)$, whereby $V(t_i^j)$ is the distribution function of the phase durations at the points in time j=8, 9 and 10, as designated in FIG. 1. In general, the p-quantiles can be defined as a function of the probability of the distribution function $V(t_i^j)$, i.e., $p=F(V(t_i^j))$.

As an alternative, assuming a Gaussian amplitude distribution, the threshold can be defined as $\mu(t_i^j)+Q(V(t_i^j))*\sigma(t_i^j)$ with $\mu(t_i^j)$ as the mean value and $\sigma(t_i^j)$ as the standard deviation of the amplitude distribution at the point in time $t_i^j$. $Q(V(t_i^j))$ is a factor that depends on the probability of the distribution function $(V(t_i^j))$. If the amplitude distribution is limited to an interval between $\mu-/+2.5\sigma$, thus $Q=-2.5+(1-V(t_i^j))*5$. For very low probability values $V(t_i^j)$ is Q=2.5 and thus the threshold is relatively high at $\mu(t_i^j)+2.5*\sigma(t_i^j)$. In case of high probabilities (close to 1), there is a low threshold at $\mu(t_i^j)-2.5*\sigma(t_i^j)$.

Figure 2:
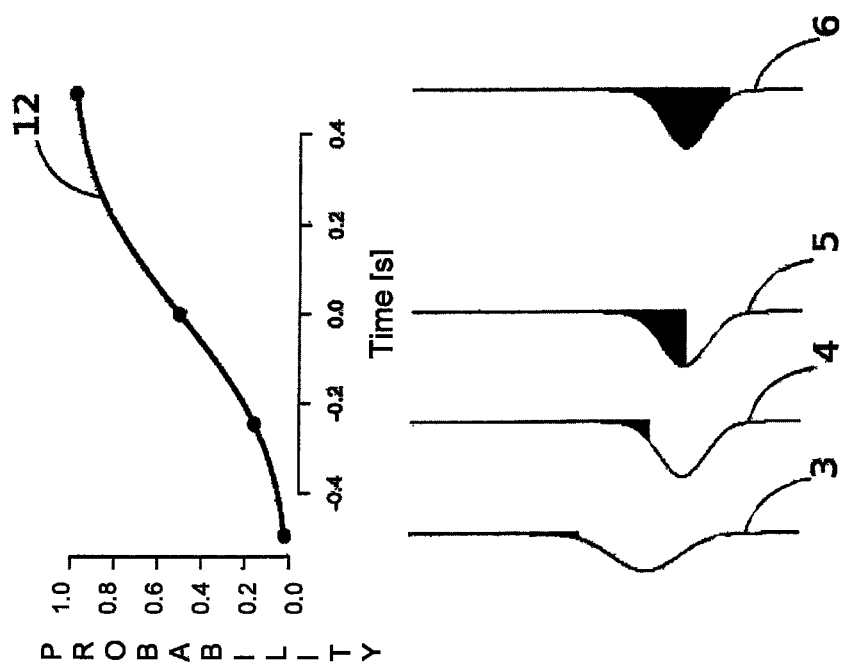
FIG. 2 is a graphical representation showing a breathing activity signal as a function of time with associated threshold curves.

Clearly, this means that the threshold at point in time $t_{i1}$ at the uppermost edge of the set of curves of breathing activity signals beginning in this case during the transition at point in time $t_{im}$ continuously undercuts into the amplitude distributions of the breathing activity signals in the histograms 3, 4 and 5, as indicated in FIG. 1 and FIG. 2 by the shaded parts of the distributions, which show the amplitudes of the breathing activity signal exceeding the inspiratory threshold. At the point in time $t_{im}$ of the mean phase duration with $V(t_{im})=0.5$, the threshold lies, such that it forms the median or the 0.5-quantile of the amplitude distribution of the breathing activity signal at the point in time $t_{im}$. Correspondingly, the threshold then lies centrally in distribution 5. After reaching the mean phase duration $t_{im}$, it is not meaningful to adjust the threshold further to histograms of the amplitude distributions at later points in time, since increasingly influences of breathing activity signals would also be contained in these later histograms, which come from inspirations already begun again. Hence, the threshold is now lowered down to the expected phase duration maximum $t_{i2}$, designated by 11 in FIG. 1, to the threshold target value. The threshold target value, as described above for the points in time $t_i^j$, is determined as a quantile, or assuming a Gaussian distribution, as a multiple of standard deviation relative to the mean value, but in relation to the amplitude distribution at the point in time $t_{im}$. The expected phase duration maximum $t_{i2}$ may be fixed above the mean value by a number of standard deviations, which correspond to a preset probability that a phase duration maximum lies before the fixed phase endpoint, whereby the preset probability is at least 0.8.

During an inspiration phase, i.e., for the detection of the next expiration, the dynamic expiratory threshold runs corresponding to the above-described pattern, with the exception that it is held at low values until the end of the expiratory refractory period $t_{e1}$ and is then raised monotonically, increasing to an expiratory threshold target value, i.e., the threshold runs, inversely to FIGS. 1 and 2 at the bottom, into the distributions, until it lies at the median value of the expiration phase durations $t_{eM}$ centrally in the distribution of the amplitudes of the breathing activity signal, after which it is raised monotonically, increasing to the expiratory threshold target value. The threshold target value is, as described above, determined as a quantile or, assuming a Gaussian distribution, as a multiple of the standard deviation relative to the mean value, but in relation to the amplitude distribution at the point in time $t_{em}$.

Figure 3:
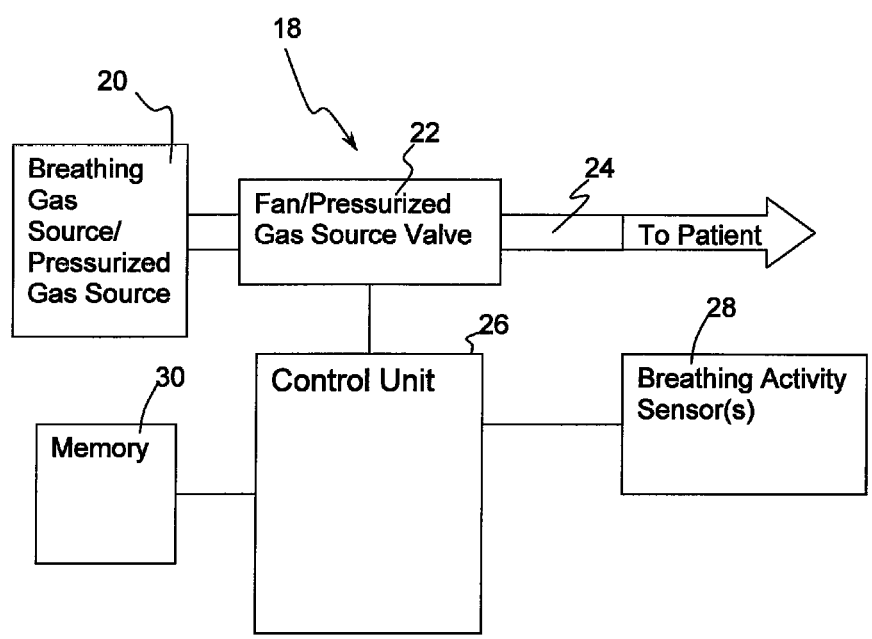
FIG. 3 is a schematic view of a respirator according to the invention.

FIG. 3 shows a respirator 18 with a breathing gas source/pressurized gas source 20 connected to a fan/controllable respiratory gas pressure supply valve 22 for conveying breathing gas through connection lines 24 to a patient. A control unit 26 has a memory or is connected to a memory 30. The control unit 26 controls the fan/valve 22. Sensors 28 are connected to the control unit 26 for picking up a breathing activity signal. The control unit controls the respirator in accordance with the described process for a consecutively made changeover between inspiration and expiration phases of respiration.

While specific embodiments of the invention have been shown and described in detail to illustrate the application of the principles of the invention, it will be understood that the invention may be embodied otherwise without departing from such principles.

What is claimed is:

1. A process for automatic control of a respirator to change over alternately between inspiration and expiration phases of respiration, the process comprising the steps of:

checking a detected respiratory breathing activity signal, with a control unit, in a phase of respiration for a threshold criterion for changing over into a next phase of respiration and if the threshold criterion is met, a changeover is made from one phase of respiration into the other;

using, in an expiration phase, an inspiration dynamic threshold curve $u_{insp,thresh}(t)$ for changing over into an inspiration phase, which inspiration dynamic threshold curve $u_{insp,thresh}(t)$ is held, after a beginning of a present expiration phase, at high values until an end of a selected inspiratory refractory period $t_{i1}$ in order to prevent a changeover into inspiration, and then is lowered monotonically, dropping to an inspiratory threshold target value at an expected point in time of a phase duration maximum $t_{i2}$ of a present expiration phase and is then changed over into the inspiration phase when the breathing activity signal exceeds the inspiration dynamic threshold curve $u_{insp,thresh}(t)$;

using, in an inspiration phase, an expiration dynamic threshold curve $u_{exp,thresh}(t)$ for changing over into an expiration phase, which expiration dynamic threshold curve $u_{exp,thresh}(t)$ is held, after a beginning of a present inspiration phase, at low values until an end of a selected expiratory refractory period $t_{e1}$ in order to prevent a changeover into expiration, and then is raised monotonically, increasing to an expiratory threshold target value at an expected point in time of a phase duration maximum $t_{e2}$ of the present inspiration phase and is then changed over into the expiration phase when the breathing activity signal drops below the expiration dynamic threshold curve $u_{exp,thresh}(t)$;

storing a phase duration of inspiration and expiration phases or breath duration comprising inspiration and expiration phases;

deriving expected points in time of the phase duration maximum $t_{i2}$ and the phase duration maximum $t_{e2}$ from distributions of phase durations in relation to a beginning of a respective phase of respiration or from a distribution of the breath durations in relation to a beginning of the previous phase of respiration; and controlling the respirator with said control unit based on the above process steps such that the respirator controls the delivery of breathing gas to a patient.

2. A process in accordance with claim 1, wherein an expected phase duration maximum $t_{i2}$ and phase duration maximum $t_{e2}$ are derived from the distributions of phase durations of the inspiration and expiration phases or distribution of breath durations as a P-quantile of these distributions, whereby parameters $P_{i2}$ and $P_{e2}$ are determined for the quantiles beforehand, and parameter values $P_{i2}$ and $P_{e2}$ are at least 0.8.

3. A process in accordance with claim 1, wherein an expected phase duration maximum $t_{i2}$ and phase duration maximum $t_{e2}$ are derived from the distributions of phase durations of the inspiration and expiration phases or distribution of breath durations under the assumption that the distributions follow a Gaussian distribution, and the expected phase duration maximum $t_{i2}$ are fixed above the mean value by a number of standard deviations, which correspond to a preset probability that a phase duration maximum lies before a fixed phase endpoint, whereby the preset probability is at least 0.8.

4. A process in accordance with claim 1, wherein points in time of an end of inspiratory and expiratory refractory periods $t_{i1}$ and $t_{e1}$ and expected points in time of the phase duration maximum $t_{i2}$ and phase duration maximum $t_{e2}$ are related to a point in time of changeover into a present phase of respiration.

5. A process in accordance with claim 1, wherein a pattern of the breathing activity signal is stored over at least a duration of a half phase of respiration and a beginning of a present phase of respiration is determined by examining a breathing activity signal pattern within a period about a point in time of the changeover into a present phase of respiration, and points in time of an end of the inspiratory refractory period $t_{i1}$ and the expiratory refractory period $t_{e1}$ and the expected points in time of the phase duration maximum $t_{i2}$ and phase duration maximum $t_{e2}$ are related to the determined point in time of the beginning of the present phase of respiration.

6. A process in accordance with claim 1, wherein points in time of the end of the inspiratory refractory period $t_{i1}$ and/or the expiratory refractory period $t_{e1}$ are each derived from distributions of the phase durations of the inspiration and expiration phases as a p-quantile of said distributions, whereby the p-quantile values used here $p_{i1}$ and $p_{e1}$ are selected beforehand and have values of less than 1.

7. A process in accordance with claim 1, wherein values of the breathing activity signal are stored at a plurality of points in time $t_i^j \in [t_{i1},t_{im}]$ and $t_e^k \in [t_{e1},t_{em}]$ (j=1,...m and k=1,...m), whereby $t_{im}$ and $t_{em}$ correspond to the points in time of median values of distributions of the inspiratory and expiratory phase durations and are accumulated as amplitude distributions of the signal values of the breathing activity signal at said plurality of points in time, and the inspiratory and expiratory thresholds are fixed in the amplitude distributions, such that the probability of changeover according to the distribution function of the phase durations at points in time $t_i^j \in [t_{i1},t_{im}]$ and $t_e^k \in [t_{e1},t_{em}]$ follows the probability, with which the threshold criterion for changeover is met according to the amplitude distributions at the points in time $t_i^j$ and $t_e^k$.

8. A process in accordance with claim 7, wherein the inspiratory threshold $u_{insp,thresh}(t_i^j)$ is fixed such that the inspiratory threshold $u_{insp,thresh}(t_i^j)$ forms a p-quantile with $p=F_1(V(t_i^j))$ in the breathing activity signal distribution at the point in time $t_i^j$, whereby $F_1(V(t_i^j))$ is a predetermined function of the distribution function of phase durations, after which the inspiratory threshold is lowered, such that the inspiratory threshold reaches the inspiratory threshold target value at an expected phase duration maximum $t_{i2}$, and the expiratory threshold $u_{exp,thresh}(t_e^k)$ is fixed such that the expiratory threshold $u_{exp,thresh}(t_e^k)$ forms a p-quantile with $p=F_2(V(t_e^k))$ in the breathing activity signal distribution at point in time $t_e^k$, whereby $F_2(V(t_e^k))$ is a predetermined function of the distribution function of the phase durations, after which the expiratory threshold is raised, such that the expiratory threshold reaches the expiratory threshold target value at an expected phase duration maximum $t_{e2}$.

9. A process in accordance with claim 8, wherein $F_1(V(t_i^j))=1-V(t_i^j)$ and $F_2(V(t_e^k))=V(t_e^k)$ is defined beforehand.

10. A process in accordance with claim 7, wherein assuming a Gaussian amplitude distribution, the inspiratory threshold is defined as $\mu(t_i^j)+Q(V(t_i^j))*\sigma(t_i^j)$, wherein $\mu(t_i^j)$ is the mean value and $\sigma(t_i^j)$ is the standard deviation of the amplitude distribution at the point in time $t_i^j$ and $Q(V(t_i^j))$ is a factor with preselected dependence on the distribution function $V(t_i^j)$, after which the inspiratory threshold is lowered, such that the inspiratory threshold reaches the inspiratory threshold target value at an expected phase duration maximum $t_{i2}$, and, assuming Gaussian amplitude distributions, the expiratory threshold is defined as $\mu(t_e^k)+Q(V(t_e^k))*\sigma(t_e^k)$, wherein $\mu(t_e^k)$ is the mean value and $\sigma(t_e^k)$ is the standard deviation of the amplitude distribution at the point in time $t_e^k$ and $Q(V(t_e^k))$ is a factor with preselected dependence on the distribution function $V(t_e^k)$, after which the expiratory threshold is raised, such that the expiratory threshold reaches the expiratory threshold target value at an expected phase duration maximum $t_{e2}$.

11. A process in accordance with claim 7, wherein a curve of inspiratory and expiratory thresholds is interpolated between consecutive points in time $t_i^j$ and $t_e^k$, respectively.

12. A process for control of a respirator to change over between inspiration and expiration phases of respiration, the process comprising the steps of:

receiving a respiratory breathing activity signal, with a control unit, during a phase of respiration;

changing over from a phase of respiration into another phase of respiration if a threshold criterion is met;

during each expiration phase, using a inspiration dynamic threshold curve $u_{insp,thresh}(t)$ as the threshold criterion for changing over into an inspiration phase, the inspiration dynamic threshold curve $u_{insp,thresh}(t)$ having high values until an end of a selected inspiratory refractory period $t_{i1}$ in order to prevent a changeover into inspiration, and then having lowered inspiratory threshold target values closer to an expected point in time of a phase duration maximum $t_{i2}$ of a present expiration phase;

during each inspiration phase, using a expiration dynamic threshold curve $u_{exp,thresh}(t)$ as the threshold criterion for changing over into an expiration phase, the expiration dynamic threshold curve $u_{exp,thresh}(t)$ having low values until an end of a selected expiratory refractory period $t_{e1}$ in order to prevent a changeover into expiration, and then having lowered expiratory threshold target values closer to an expected point in time of a phase duration maximum $t_{e2}$ of a present inspiration phase;

storing a phase duration of inspiration and expiration phases or breath duration comprising inspiration and expiration phases;

deriving expected points in time of the phase duration maximum $t_{i2}$ and phase duration maximum $t_{e2}$ from distributions of phase durations in relation to a beginning of a respective phase of respiration or from a distribution of the breath durations in relation to a beginning of the previous phase of respiration; and controlling the respirator with said control unit based on the above process steps such that the respirator controls the delivery of breathing gas to a patient.

13. A process in accordance with claim 12, wherein an expected phase duration maximum $t_{i2}$ and phase duration maximum $t_{e2}$ are derived from the distributions of phase durations of the inspiration and expiration phases or distribution of breath durations as a P-quantile of these distributions, whereby parameters $P_{i2}$ and $P_{e2}$ are determined for the quantiles beforehand, and the parameter values $P_{i2}$ and $P_{e2}$ are at least 0.8.

14. A process in accordance with claim 12, wherein an expected phase duration maximum $t_{i2}$ and phase duration maximum $t_{e2}$ are derived from the distributions of phase durations of the inspiration and expiration phases or distribution of breath durations under the assumption that the distributions follow a Gaussian distribution, and the expected phase duration maximum $t_{i2}$ are fixed above a mean value by a number of standard deviations, which correspond to a preset probability that a phase duration maximum lies before a fixed phase endpoint, whereby the preset probability is at least 0.8.

15. A process in accordance with claim 12, wherein points in time of an end of inspiratory and expiratory refractory periods $t_{i1}$ and $t_{e1}$ and expected points in time of the phase duration maximum $t_{i2}$ and phase duration maximum $t_{e2}$ are related to a point in time of changeover into a present phase of respiration.

16. A process in accordance with claim 12, wherein a pattern of the breathing activity signal is stored over at least a duration of a half phase of respiration and a beginning of a present phase of respiration is determined by examining the breathing activity signal pattern within a period about a point in time of the changeover into a present phase of respiration, and points in time of an end of the inspiratory refractory period $t_{i1}$ and the expiratory refractory period $t_{e1}$ and the expected points in time of the phase duration maximum $t_{i2}$ and phase duration maximum $t_{e2}$ care related to the determined point in time of the beginning of the present phase of respiration.

17. A process in accordance with claim 12, wherein points in time of the end of the inspiratory refractory period $t_{i1}$ and/or the expiratory refractory period $t_{e1}$ are each derived from distributions of the phase durations of the inspiration and expiration phases as a p-quantile of said distributions, whereby the p-quantile values used $p_{i1}$ and $p_{e1}$ are selected beforehand and have values of less than 1.

18. A process in accordance with claim 12, wherein values of the breathing activity signal are stored at a plurality of points in time $t_i^j \in [t_{i1}, t_{im}]$ and $t_e^k \in [t_{e1}, t_{em}]$ (j=1, ... m and k=1, ... m), whereby $t_{im}$ and $t_{em}$ correspond to the points in time of median values of distributions of the inspiratory and expiratory phase durations and are accumulated as amplitude distributions of the signal values of the breathing activity signal at this plurality of points in time, and the inspiratory and expiratory thresholds are fixed in the amplitude distributions, such that the probability of changeover according to the distribution function of the phase durations at points in time $t_i^j \in [t_{i1}, t_{im}]$ and $t_e^k \in [t_{e1}, t_{em}]$ follows the probability, with which the threshold criterion for changeover is met according to the amplitude distributions at the points in time $t_i^j$ and $t_e^k$.

19. A process in accordance with claim 18, wherein the inspiratory threshold $u_{insp,thresh}(t_i^j)$ is fixed such that the inspiratory threshold $u_{insp,thresh}(t_i^j)$ forms a p-quantile with $p=F_1(V(t_i^j))$ in the breathing activity signal distribution at the point in time $t_i^j$, whereby $F_1(V(t_i^j))$ is a predetermined function of the distribution function of phase durations, after which the inspiratory threshold is lowered, such that the inspiratory threshold reaches the inspiratory threshold target value at an expected phase duration maximum $t_{i2}$, and the expiratory threshold $u_{exp,thresh}(t_e^k)$ is fixed such that the expiratory threshold $u_{exp,thresh}(t_e^k)$ forms a p-quantile with $p=F_2(V(t_e^k))$ in the breathing activity signal distribution at point in time $t_e^k$, whereby $F_2(V(t_e^k))$ is a predetermined function of the distribution function of the phase durations, after which the expiratory threshold is raised, such that the expiratory threshold reaches the expiratory threshold target value at an expected phase duration maximum $t_{e2}$.

20. A process in accordance with claim 18, wherein assuming a Gaussian amplitude distribution, the inspiratory threshold is defined as $\mu(t_i^j)+Q(V(t_i^j))*\sigma(t_i^j)$, wherein $\mu(t_i^j)$ is a mean value and $\sigma(t_i^j)$ is the standard deviation of the amplitude distribution at the point in time $t_i^j$ and $Q(V(t_i^j))$ is a factor with preselected dependence on the distribution function $V(t_i^j)$, after which the inspiratory threshold is lowered, such that the inspiratory threshold reaches the inspiratory threshold target value at an expected phase duration maximum $t_{i2}$, and, assuming Gaussian amplitude distributions, the expiratory threshold is defined as $\mu(t_e^k)+Q(V(t_e^k))*\sigma(t_e^k)$, wherein $\mu(t_e^k)$ is the mean value and $\sigma(t_e^k)$ is the standard deviation of the amplitude distribution at the point in time $t_e^k$ and $Q(V(t_e^k))$ is a factor with preselected dependence on the distribution function $V(t_e^k)$, after which the expiratory threshold is raised, such that the expiratory threshold reaches the expiratory threshold target value at an expected phase duration maximum $t_{e2}$.

* * * * *